(12) United States Patent
Blanvalet et al.

(10) Patent No.: US 8,506,698 B2
(45) Date of Patent: Aug. 13, 2013

(54) ORAL COMPOSITIONS AND METHODS

(75) Inventors: Claude Blanvalet, Liege (BE); Pierre Lambert, Fleron (BE); Viviane Tack, Soumagne (BE)

(73) Assignee: Colgate-Palmolive Company, New York, NY (US)

( * ) Notice: Subject to any disclaimer, the term of this patent is extended or adjusted under 35 U.S.C. 154(b) by 0 days.

(21) Appl. No.: 12/936,338

(22) PCT Filed: Apr. 6, 2009

(86) PCT No.: PCT/US2009/039655
§ 371 (c)(1),
(2), (4) Date: Oct. 4, 2010

(87) PCT Pub. No.: WO2009/124311
PCT Pub. Date: Oct. 8, 2009

(65) Prior Publication Data
US 2011/0033394 A1    Feb. 10, 2011

Related U.S. Application Data

(60) Provisional application No. 61/042,470, filed on Apr. 4, 2008.

(51) Int. Cl.
*A61K 8/21*  (2006.01)
*A61K 8/27*  (2006.01)
*A61K 8/24*  (2006.01)
*A61K 8/69*  (2006.01)
*A61Q 11/00* (2006.01)

(52) U.S. Cl.
USPC .............. 106/35; 106/657; 424/52; 424/53; 424/485

(58) Field of Classification Search
USPC .......................... 260/97; 523/115; 424/481
See application file for complete search history.

(56) References Cited

U.S. PATENT DOCUMENTS

| | | | |
|---|---|---|---|
| 2,834,770 A * | 5/1958 | Kalkhof-Rose | 530/201 |
| 3,538,230 A | 11/1970 | Pader et al. | |
| 3,689,637 A | 9/1972 | Pader | |
| 3,711,604 A | 1/1973 | Colodney et al. | |
| 3,911,104 A | 10/1975 | Harrison | |
| 3,935,306 A | 1/1976 | Roberts et al. | |
| 4,040,858 A | 8/1977 | Wason | |
| 6,083,421 A | 7/2000 | Huang et al. | |
| 6,348,217 B1 | 2/2002 | Santos et al. | |
| 6,652,280 B2 * | 11/2003 | Cohen | 433/217.1 |
| 2002/0006600 A1 | 1/2002 | Cohen | |
| 2005/0175552 A1 * | 8/2005 | Hoic et al. | 424/49 |
| 2005/0196358 A1 * | 9/2005 | Georgiades et al. | 424/53 |
| 2007/0183986 A1 | 8/2007 | Allred et al. | |

FOREIGN PATENT DOCUMENTS

| | | |
|---|---|---|
| DE | 2004000552 | 8/2005 |
| EP | 0815831 | 1/1998 |
| EP | 1666019 | 6/2006 |
| GB | 1383281 | 2/1974 |
| JP | 11 116452 | 4/1999 |
| JP | 2001-302428 A | 10/2001 |
| RU | 2131242 | 6/1999 |
| TW | 200605913 | 2/2006 |
| WO | WO 02/11671 | 2/2002 |

OTHER PUBLICATIONS

International Search Report and Written Opinion for International Application No. PCT/US2009/039655 mailed on Aug. 4, 2009.
Hoang-Dao B T et al: "Evaluation of a natural resin-based new material (Shellac F) as a potential desensitizing agent" Dental Materials, Elsevier, vol. 24, No. 7, Jul. 1, 2008, pp. 1001-1007, XP022671158.
"Kariesinsidens otter to ars bruk av de fluorholdige lakkene Duraphat og Carex. (Two-year trial of the fluoride-containing varnishes Duraphat and Carex.)—Nord A. and Haugejorden O. (1991) Nor. Tannlegeforen. Tid. 101, 46-49" Journal of Dentistry, Elsevier, vol. 20, No. 6, Dec. 1, 1992, p. 380, XP023107391.
Database WPI Week 200027 Thomson Scientific, London, GB; AN 2000-315981 XP002538456 & RU 2 131 242 C1 (Lukinykh L M) Jun. 10, 1999.
Database WPI Week 200223 Thomson Scientific, London, GB; AN 2002-178158 XP002538457 & KR 2001 089 957 A (LG Chem Investment Ltd) Oct. 17, 2001.
Azouka et al., 1993, "The Production of Shellac and Its General and Dental Uses: A Review," J. Oral Rehabilitation 20:393-400.
Frosin, 1974, *The Great Soviet Encyclopedia*, Moscow [Sovetskaya Entsiklopediya] Third Edition, vol. 16, p. 161, col. 469.

* cited by examiner

*Primary Examiner* — Walter Webb
(74) *Attorney, Agent, or Firm* — Howard C. Lee

(57) ABSTRACT

An oral composition comprising an active component and an adhesive film forming component comprising bleached shellac and shellac wax for the treatment of teeth.

17 Claims, 2 Drawing Sheets

ORAL COMPOSITIONS AND METHODS

CROSS-REFERENCE TO RELATED PATENT APPLICATIONS

The present application is a national stage entry under 35 U.S.C. §371 of International Patent Application No. PCT/US2009/039655, filed Apr. 6, 2009, which in turn claims the benefit of U.S. Provisional Patent Application No. 61/042,470, filed Apr. 4, 2008, the entireties of which are hereby incorporated by reference.

BACKGROUND OF THE INVENTION

Dental caries is a major dental disease that affects the majority of the population. In the early part of the 20th century, investigators discovered that fluoride was effective in reducing the incidence of caries. Since that time, fluoride research has developed, and it is now well accepted that fluoride treatments benefit dental health.

Fluoride compositions are routinely applied to teeth by any number of methods and compositions, the most common methods by utilizing fluoride containing dentifrice compositions, such as toothpastes and mouthwashes. However, there are certain situations where it is desirable to have prolonged contact of the fluoride compositions with teeth, and to use amounts of fluoride that exceed fluoride amounts present in dentifrice compositions. For example, it may be desirable to treat xerostomia (dry mouth), tooth hypersensitivity, dental caries with high levels of fluoride for prolonged periods of time. This may be accomplished by the use of a dental tray, wherein a composition is applied to the dental tray, and then the composition and tray are applied to the teeth to be treated; however, this method is inconvenient, as the user is forced to retain the tray in their mouth during use, and thus the treatment time is limited by how long the user may retain the tray in their mouth. Thus, tooth varnish compositions have been developed to be applied directly to the tooth with a brush. The use of tooth varnish compositions are well known in the art, and the varnish compositions allow for a longer exposure time (e.g., about or greater than 2 hours) before the composition is worn away.

Existing tooth varnish compositions generally contain an active component, e.g., to treat caries, provide fluoride therapy, treat xerostomia, tooth sensitivity, and/or whiten or bleach teeth, and an adhesive film forming component to cause the active material to adhere to the tooth. However, due to the colour of the adhesive film forming component, the varnish may cause a temporary change in the surface colour of teeth, e.g., creating a yellow color. A color difference may be desirable in that it aids the user in identifying tooth surfaces on which the varnish has been applied; however, excessive color is undesirable, as yellow teeth suggest an unhygienic oral cavity, regardless of how temporary the varnish is. Additionally, the discoloration may cause embarrassment to the user, as others may realize that the user is utilizing a tooth varnish. Thus, there is a need to develop tooth varnish compositions which do not adversely affect the colour of a tooth.

Another disadvantage with tooth varnishes is that the varnishes tend to be multiphase, e.g., as the active component is insoluble in the adhesive film forming phase, and the varnish may separate out into distinct phases. Additionally, components of the adhesive film forming phase, may also separate into distinct phases over time. Users typically need to stir the varnish in order to mix the phases, which is time consuming and wasteful, as the varnish adheres to the mixing apparatus and is then discarded. Thus, there exists a need to develop tooth varnish compositions with greater stability, wherein the phases do not readily separate.

BRIEF SUMMARY OF THE INVENTION

In accordance with the present invention, it has been surprisingly discovered that a tooth varnish comprising an active component, and an adhesive film forming component comprising shellac wax and a bleached shellac imparts less color when applied to a tooth, and has greater stability, e.g., the phases tend not to separate; moreover, the use of such compositions does not cause a reduction of activity of the active component. The varnish may be easily applied by brush, e.g., dipping a brush into the composition, and then applying it to a tooth surface, preferably a dry tooth surface. The varnish is temporary, and wears off of the tooth surface after a period of time, e.g., within 48 hours of application, within 24 hours of application, within 12 hours of application, within 6 hours of application, or within 2 hours of application.

Thus, the present invention is directed to composition 1.0, an oral composition comprising an active component, and adhesive film forming component comprising a bleached shellac and shellac wax.

Additional compositions of the present invention include compositions:

1.1 Composition 1.0 wherein the bleached shellac is a dewaxed bleached shellac;
1.2 Composition 1.0 or 1.1 wherein the bleached shellac comprises from about 5% to about 70% weight of the composition, e.g., from about 5% to about 40%, from about 10% to about 30%, or about 20%, or wherein the bleached shellac comprises from about 10% to about 50% by weight of the adhesive film forming component, e.g., from about 15% to about 35%, or about 25% by weight of the component;
1.3 Any of the preceding compositions wherein the shellac wax comprises from about 0.1% to about 20% weight of the composition, e.g., from about 0.5% to about 15%, from about 1% to about 10%, or about 1%, 4%, 6%, 8%, or 10%, or wherein the shellac wax comprises from about 0.1 to about 10% by weight of the adhesive film forming component, e.g., from about 0.5% to about 8%, from about 1% to about 5%, or about 2, 3, or 4%;
1.4 Any of the preceding compositions wherein the active component comprises form about 3% to about 50% by weight of the composition, e.g., from about 5% to about 30%, from about 10% to about 20%, or about 14% or 15%;
1.5 Any of the preceding compositions wherein the adhesive film forming component further comprises beeswax, colophonium, mastic, a water-insoluble alkyl cellulose, and combinations thereof;
1.6 Any of the preceding compositions wherein the adhesive film forming component comprises from about 5% to about 97% weight of the composition, e.g., from about 50% to about 95%, from about 60% to about 90%, from about 70% to about 85%, or about 80%;
1.7 Any of the preceding compositions further comprises a solvent, e.g., wherein the composition comprises from about 5% to about 50% weight of the solvent, e.g., from about 10% to about 40%, from about 25% to about 30%, or about 27%;
1.8 Any one of the preceding compositions wherein the active component comprises a solvent, e.g., wherein the solvent is from about 20% to about 60% by weight of the active component, e.g., from about 30% to about 50%, from about 35% to about 45%, or about 40% or 43%;

1.9 Compositions 1.7 or 1.8 wherein the solvent is selected from methanol, ethanol, ethyl acetate, acetone, isopropyl alcohol, or combinations thereof;

1.10 Any of the preceding compositions wherein the active component comprises colophonium, e.g., wherein the active component comprises from about 5% to 40% colophonium by weight, e.g., from about 10% to about 30%, from about 15% to about 25%, or about 20 or 22%;

1.11 Any of the preceding compositions wherein the active component comprises a fluoride ion source, e.g., present in an amount of about 0.5% to about 15% by weight of the total composition, e.g., from about 1% to about 10%, from about 2% to about 7%, or about 5%;

1.12 Any of the preceding compositions comprising a fluoride ion source sufficient to provide from about 1,000 ppm to about 50,000 ppm fluoride ions in the composition, e.g., about 22,000 ppm, or 23,000 ppm;

1.13 Any of the preceding compositions comprising a fluoride ion source selected from sodium fluoride, potassium fluoride, calcium fluoride, zinc fluoride, zinc ammonium fluoride, lithium fluoride, ammonium fluoride, stannous fluoride, stannous fluorozirconate, sodium monofluorophosphate, potassium monofluorophosphate, laurylamine hydrofluoride, diethylaminoethyloctoylamide hydrofluoride, didecyldimethylammonium fluoride, cetylpyridinium fluoride, dilaurylmorpholinium fluoride, sarcosine stannous fluoride, glycine potassium fluoride, glycine hydrofluoride, amine fluoride, or combinations thereof;

1.14 Any of compositions wherein the active component comprises a tooth desensitizing agent;

1.15 Any of the preceding compositions comprising a tooth desensitizing agent selected from a potassium salt, capsaicin, eugenol, a strontium salt, a zinc salt, a chloride salt, or combinations thereof;

1.16 Any of the preceding compositions wherein the active component comprises an effective amount of a antibacterial agent;

1.17 Any of the preceding compositions wherein the active component comprises a tooth whitening compound;

1.18 Any of the preceding compositions substantially free of water, e.g., less than 1% by weight water;

1.19 Any of the preceding compositions comprising stannous ion agent, triclosan, triclosan monophosphate, chlorhexidine, alexidine, hexetidine, sanguinarine, benzalkonium chloride, salicylanilide, arginate esters, ethyl lauryl arginate, bisphenols, domiphen bromide, tetradecylpyridinium chloride, N-tetradecyl-4-ethylpyridinium chloride, octenidine, delmopinol, octapinol, nisin, zinc ion agent, copper ion agent, essential oils, furanones, bacteriocins, a basic amino acid, or combinations thereof;

1.20 Any of the preceding compositions which is a tooth varnish.

The present invention is also directed to a method for treating a tooth with an active component comprising applying any one of compositions 1.0-1.20 to the tooth in the oral cavity, e.g., by a brush, swab, or syringe. The present invention is also directed to methods to treat dental caries, xerostomia, tooth hypersensitivity, or dental stains comprising applying any one of compositions 1.0-1.20 to the tooth in the oral cavity. The compositions of the present invention may be applied to the enamel, dentin or cementum of the tooth and can be used to help prevent and/or treat tooth decay, remineralize the tooth surface, and hypersensitivity. Preferably, the composition remains adhered to the tooth surface for 0.5 hours to 48 hours following application, e.g., for 2, 4, 6, 12, or 14 hours following application.

DETAILED DESCRIPTION OF THE INVENTION

Figure 1:
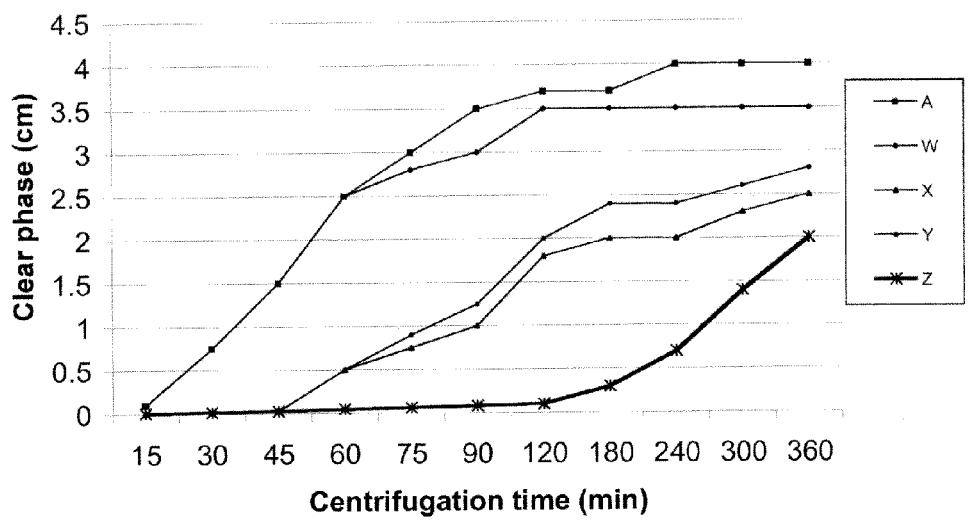
FIG. 1 details results as described in Example 2.

Throughout the present disclosure, ranges are used as a shorthand for describing each and every value that is within the range. Any value within the range can be selected as the terminus of the range.

The active component of the present invention may be any oral active which is known in the art, e.g., fluoride ion sources, antibacterials, tooth whitening and/or bleaching agents, and antisensitivity agents.

The adhesive film forming component of the present invention is used to facilitate adhesion of the active component to the dental surface, and to form a substantially continuous film over the surface to which the present invention is applied. The adhesive film forming component contains shellac wax, bleached shellac, and optionally other adhesive or film forming materials which are known in the art.

Shellac is a processed resinous secretion from the lac insect *Kerria lacca*. Methods of manufacturing shellac are known in the art. Although shellac has previously been used in tooth varnishes, the inventors have discovered that by using a bleached shellac in a tooth varnish, the stability of the varnish is improved, and the color tooth when the varnish is applied to the tooth is also improved.

Methods of producing shellac wax are known in the art. Generally, unprocessed shellac is dissolved in an alkali solution or an alcohol, and subject to solvent extraction, optionally using activated carbon. The shellac wax is then recovered from the solvent phase. Shellac wax may be obtained from Renshel Exports Pvt. Ltd. (Kolata, India), or Sitaram Saraf (Kolkata, India).

Methods of producing bleached shellac (which may bedewaxed) are also known in the art. Generally, the solvent extracted alkali solution (produced from manufacturing shellac wax) is treated with a bleaching agent, e.g., sodium hypochlorite. The bleached shellac is precipitated from solution with a strong acid, e.g., sulphuric acid and dried. See also U.S. Pat. No. 6,348,217. Bleached shellac may be obtained from Renshel Exports Pvt. Ltd. as type 101 (Kolata, India), or Sitaram Saraf (Kolkata, India)

Other film forming materials may also be added to the film forming component. For example, white wax, beeswax, white beeswax, colophonum (also known as rosin), mastic, polybutene, and water insoluble alkyl cellulose as described in DE 20 2004 000 552 U1 may be incorporated into the adhesive film forming component. Colophonium may be obtained from Willers Engels & Co. GMBH (Hanburg, Germany).

The compositions of the present invention comprise an active component, which is selected depending on the intended purpose of the tooth varnish. For example, an active component may be a fluoride ion source for fluoride treatments, treatment of caries, hypersensitivity, or xerostomia. An active component may be an antisensitivity agent for treatment of tooth hypersensitivity. An active component may be a tooth whitening or bleaching composition for tooth whitening or bleaching, e.g., for treating stains and discolorations. The active component preferably does not react with the adhesive film forming component.

Fluoride ion sources are known in the art, and may be anything that is capable of releasing fluoride ion in an aqueous environment. Typical sources include soluble salts of the fluoride ion; such as, for example: sodium fluoride, potassium fluoride, calcium fluoride, zinc fluoride, zinc ammonium fluoride, lithium fluoride, ammonium fluoride, stannous fluoride, stannous fluorozirconate, and complex fluorides, monofluorophosphates and salts thereof such as, e.g., sodium monofluorophosphate or potassium monofluorophosphate, laurylamine hydrofluoride, diethylaminoethyloctoylamide hydrofluoride, didecyldimethylammonium fluoride, cetylpyridinium fluoride, dilaurylmorpholinium fluoride, sarcosine stannous fluoride, glycine potassium fluoride, glycine hydrofluoride, and amine fluorides. See, e.g., U.S. Pat. Nos. 3,538,230, 3,689,637, 3,711,604, 3,911,104, 3,935,306 and 4,040,858, the contents of which are herein incorporated by reference in their entirety. The fluoride ion source may be presented as a salt or a slime preparation. Preferably, the fluoride ion source is in the form of a salt, and a preferred fluoride ion source is sodium fluoride.

The fluoride ion source is most preferably in an amount such that it is capable of providing a high level of fluoride ion in the composition, that is at least about 5,000 ppm, and in some instances up to as much as 50,000 ppm, e.g., from about 7,000 ppm to about 40,000 ppm, from about 15,000 ppm to about 30,000 ppm, or about 22,000 or 23,000 ppm. In order to provide such a concentration in the optimal ppm range, the exact weight percentage of the fluoride ion source in the composition may vary, depending upon the stoichiometric properties of different fluoride ion sources.

Preferably, the antibacterial agents may be utilized as an active component if reduction of microorganisms is desired. Antibacterial agents are known in the art, and include benzoic acid, sodium benzoate, potassium benzoate, boric acid, and phenolic compounds such as betanaphthol, chlorothymol, thymol, anethole, eucalyptol, carvacrol, menthol, phenol, amylphenol, hexylphenol, heptylphenol, octylphenol, hexylresorcinol, laurylpyridinium chloride, myristylpyridinium chloride, cetlpyridinium fluoride, cetylpyridinium chloride, cetylpyridinium bromide, and halogenated diphenyl ethers, such as triclosan. Compositions of the present invention may also include one or more basic amino acids, e.g., arginine, in free base or salt form. Such agents may be added in effective amounts, e.g., from about 1% to about 20% by weight based on the total weight of the composition, depending on the agent chosen.

The compositions of the present invention may incorporate one or more antisensitivity agents, e.g., potassium salts such as potassium nitrate, potassium bicarbonate, potassium chloride, potassium citrate, and potassium oxalate; capsaicin; eugenol; strontium salts; zinc salts; chloride salts and combinations thereof. Such agents may be added in effective amounts, e.g., from about 1% to about 20% by weight based on the total weight of the composition, depending on the agent chosen. The compositions of the present invention may also be used to treat hypersensitivity by blocking dentin tubules when applied to a tooth.

The active component of the present invention may also be a tooth whitening or tooth bleaching composition, which are known in the art. Suitable whitening and bleaching composition include peroxides, metal chlorites, persulfates. Peroxides include hydroperoxides, hydrogen peroxide, peroxides of alkali and alkaline earth metals, organic peroxy compounds, peroxy acids, and mixtures thereof. Peroxides of alkali and alkaline earth metals include lithium peroxide, potassium peroxide, sodium peroxide, magnesium peroxide, calcium peroxide, barium peroxide, and mixtures thereof. Other peroxides include perborate, urea peroxide, and mixtures thereof. Suitable metal chlorites may include calcium chlorite, barium chlorite, magnesium chlorite, lithium chlorite, sodium chlorite, and potassium chlorite. Such agents may be added in effective amounts, e.g., from about 1% to about 20% by weight based on the total weight of the composition, depending on the agent chosen.

The present invention may optionally include a solvent, which rapidly evaporates when the compositions of the present invention are applied to the teeth. Suitable solvents may include methanol, ethanol, ethyl acetate, acetone, or isopropanol. Preferably, the solvent is non-toxic, and a preferred solvent is ethanol. The solvent may also function as a viscosity modifier, and to ensure even deposition of the film forming component.

Preferably the composition has a viscosity of between about 100 and 5000 centipoise. In addition, the composition may also be thixotropic so that it is more easily spread during application. Due to the high viscosity and thixotropic characteristics of the composition, any tendency of the composition to otherwise run or drip once applied is minimized and/or prevented.

The oral care composition is preferably in the form of a tooth varnish, thus the compositions may be substantially free of water, e.g., 0% water, or less than 1% water by weight. It is to be understood that some ingredients in the composition, e.g., bleached shellac or ethanol, may contain trace amounts of water.

Flavors, e.g., sweeteners, may be used in the oral care compositions of the present invention if desired. Suitable sweeteners include but are not limited to: saccharins and derivatives thereof, cyclamates and derivatives thereof, acesulfane-K, thaumatin, neohisperidin dihydrochalcone, ammoniated glycyrrhizin, dextrose, levulose, sucrose, mannose, glucose, xylitol, and any other suitable sweeteners. Other flavorings are known in the art, and may include artificial flavors, or plant extracts.

The invention will now be described with respect to the following non-limiting examples:

EXAMPLE 1

A tooth varnish active component comprising 42.5% weight ethanol, 22.9% weight colophonium, and 34.6% weight sodium fluoride. The materials are mixed until homogenous.

Five different adhesive film forming components are prepared in accordance with Table 1. The ingredients are mixed until homogenous. Unless otherwise indicated, the numbers expressed as percent weight.

TABLE 1

|  | Adhesive A | Adhesive W | Adhesive X | Adhesive Y | Adhesive Z |
| --- | --- | --- | --- | --- | --- |
| Shellac | 25.7 |  |  |  |  |
| Bleached shellac |  | 24.7 | 24.2 | 23.7 | 23.2 |
| Shellac Wax |  | 1 | 1.5 | 2 | 2.5 |
| Ethanol | 24.2 | 24.2 | 24.2 | 24.2 | 24.2 |

TABLE 1-continued

|  | Adhesive A | Adhesive W | Adhesive X | Adhesive Y | Adhesive Z |
|---|---|---|---|---|---|
| Colophonium | 34.5 | 34.5 | 34.5 | 34.5 | 34.5 |
| Beeswax | 0.6 | 0.6 | 0.6 | 0.6 | 0.6 |
| Mastic | 14.2 | 14.2 | 14.2 | 14.2 | 14.2 |
| Flavor | 0.8 | 0.8 | 0.8 | 0.8 | 0.8 |

Tooth varnish compositions are then prepared by admixing the active component and adhesive film forming component. Additional ethanol and flavorings are also added to the composition. The final tooth varnish composition contains 84.3% by weight of the adhesive component, and 14.1% by weight of the active component. The final tooth varnish compositions are presented in Table 2.

TABLE 2

|  | Varnish A | Varnish W | Varnish X | Varnish Y | Varnish Z |
|---|---|---|---|---|---|
| Shellac | 21.8 |  |  |  |  |
| Bleached Shellac |  | 20.8 | 20.4 | 20 | 19.6 |
| Shellac Wax |  | 1 | 1.4 | 1.8 | 2.2 |
| Ethanol | 27 | 27 | 27 | 27 | 27 |
| Colophonium | 32.3 | 32.3 | 32.3 | 32.3 | 32.3 |
| Sodium fluoride | 4.9 | 4.9 | 4.9 | 4.9 | 4.9 |
| White beeswax | 0.5 | 0.5 | 0.5 | 0.5 | 0.5 |
| Mastic | 11.9 | 11.9 | 11.9 | 11.9 | 11.9 |
| Flavoring | 1.6 | 1.6 | 1.6 | 1.6 | 1.6 |

EXAMPLE 2

The varnish compositions of Example 1 are spun in a 15 ml centrifuge tube for 15 minutes up to 360 hours, at 3000 rpm and 35° C. to determine their stability and tendency to separate into different phases, During centrifugation, a clear phase is produced at the top of the varnish, indicating that the phases have separated. The length of the clear phase is measured, and presented in FIG. 1.

EXAMPLE 3

Figure 2:
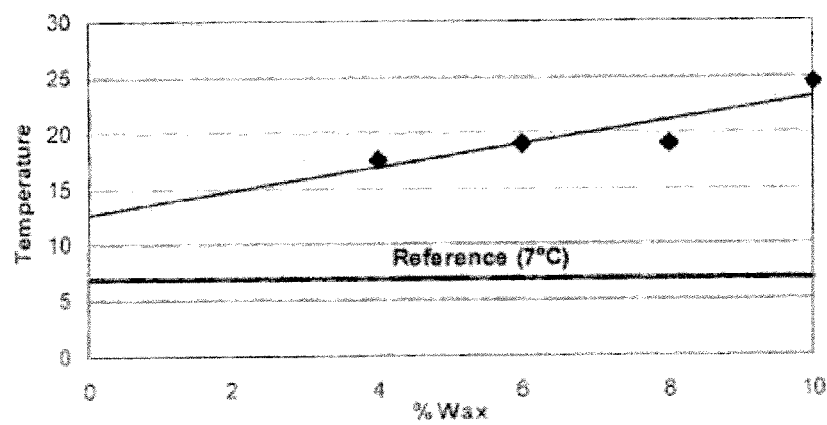
FIG. 2 details results as described in Example 3.

Varnishes W, X, Y and Z of Example 1 are subjected to increasing temperatures until a 0.1 cm phase separation is observed. The results are presented in FIG. 2, which indicates that compositions having a higher shellac wax component are stable at higher temperatures. 4%, 6%, 8%, and 10% represent varnishes W, X, Y and Z respectively.

EXAMPLE 4

Figure 3:
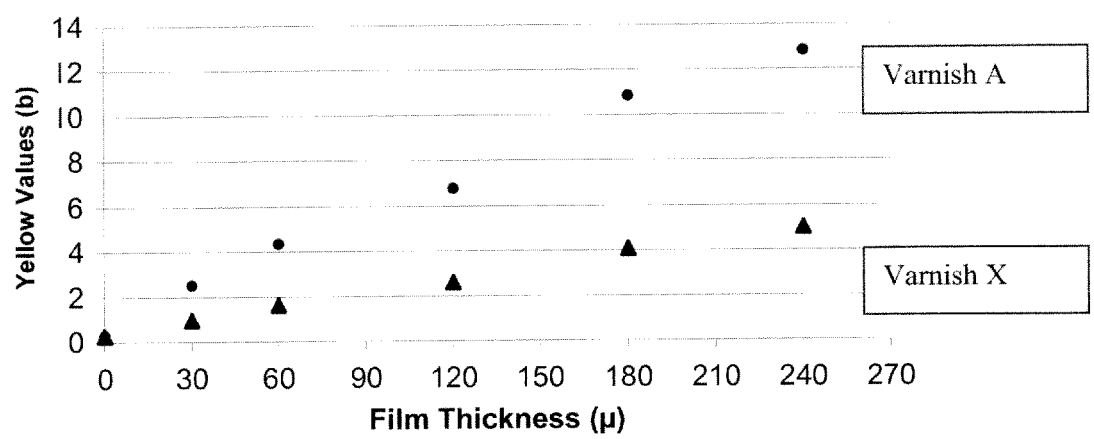
FIG. 3 details results as described in Example 4.

Varnishes A and X are applied to teeth at varying thicknesses, and the color of the teeth are evaluated according to the Hunter L, a, b Color Scale with an Ultrascan XE spectrophometer. Specifically, the b value of blue to yellow is evaluated. Results are presented in FIG. 3. It will be determined that varnish A contains a greater yellow color component than varnish X.

EXAMPLE 5

Varnishes A and X are applied by dental professionals to patient teeth to determine the degree of adhesion. It will be determined that the dental professionals found varnish X has superior adhesion properties compared to varnish A.

EXAMPLE 6

Varnishes A and X are applied by dental professionals to patient teeth to determine the ease of application. It will be found that dental professionals found that varnish X easier to apply to teeth than composition A.

It will be appreciated by those skilled in the art that changes and alterations may be made to the embodiments described above without departing from the broad inventive concept thereof. It is understood, therefore, that this invention is not limited to the particular embodiments disclosed, but it is intended to cover modifications within the spirit and scope of the present invention as defined by the appended claims.

We claim:

1. An oral composition comprising an active component, and an adhesive film forming component comprising a bleached shellac and shellac wax, wherein the oral composition is a tooth varnish and the active component comprises a fluoride ion source, an antibacterial agent, an antisensitivity agent, a tooth whitening agent, or combinations thereof, and wherein the shellac wax comprises about 0.5% to about 15% by weight of the composition.

2. The composition of claim 1 wherein the bleached shellac is a dewaxed bleached shellac.

3. The composition of claim 1 wherein the bleached shellac comprises from about 5% to about 70% weight of the composition.

4. The composition of claim 1 wherein the active component comprises form about 3% to about 50% by weight of the composition.

5. The composition of claim 1 wherein the adhesive film forming component further comprises beeswax, colophonium, mastic, a water-insoluble alkyl cellulose, and combinations thereof.

6. The composition of claim 1 wherein the adhesive film forming component comprises from about 5% to about 97% weight of the composition.

7. The composition of claim 1 wherein the composition comprises from about 5% to about 50% weight of the solvent.

8. The composition of claim 1 wherein the active component comprises colophonium and a solvent selected from the group consisting of methanol, ethanol, ethyl acetate, acetone, isopropyl alcohol, or combinations thereof.

9. The composition of claim 8 wherein the solvent is ethanol.

10. The composition of claim 1, comprising a fluoride ion source present in an amount sufficient to provide from about 1,000 ppm to about 50,000 ppm fluoride ions in the composition.

11. The composition of claim 1 wherein the fluoride ion source is selected from the group consisting of sodium fluoride, potassium fluoride, calcium fluoride, zinc fluoride, zinc ammonium fluoride, lithium fluoride, ammonium fluoride, stannous fluoride, stannous fluorozirconate, sodium monofluorophosphate, potassium monofluorophosphate, laurylamine hydrofluoride, diethylaminoethyloctoylamide hydrofluoride, didecyldimethylammonium fluoride, cetylpyridinium fluoride, dilaurylmorpholinium fluoride, sarcosine stannous fluoride, glycine potassium fluoride, glycine hydrofluoride, amine fluoride, and combinations thereof.

12. The composition of claim 11 wherein the fluoride ion source is sodium fluoride.

13. The composition of claim 1 wherein the active component comprises a halogenated diphenyl ether.

14. The composition of claim 1 which is substantially free of water.

15. A method to treat a tooth with fluoride comprising applying the composition of claim 1 to a tooth for an effective amount of time.

16. The method of claim 15 wherein the composition remains on the tooth for at least 24 hours.

17. The method of claim 15 wherein the composition is applied to a plurality of teeth.

* * * * *